(12) United States Patent
Migdal et al.

(10) Patent No.: US 7,229,951 B2
(45) Date of Patent: Jun. 12, 2007

(54) ORGANO-IMIDO MOLYBDENUM COMPLEXES AS FRICTION MODIFIER ADDITIVES FOR LUBRICANT COMPOSITIONS

(75) Inventors: Cyril A. Migdal, Pleasant Valley, NY (US); Paul E. Stott, Southbury, CT (US); Nikolai Aleksandrovich Ustynyuuk, Moscow (RU); Dmitry Nikolaievich Zaroubine, Tatarstan (RU); Ilia Victorovich Yampolsky, Moscow (RU); Konstantin Aleksandrovich Rufanov, Berlin (DE)

(73) Assignee: Crompton Corporation, Middlebery, CT (US)

( * ) Notice: Subject to any disclaimer, the term of this patent is extended or adjusted under 35 U.S.C. 154(b) by 555 days.

(21) Appl. No.: 10/483,342

(22) PCT Filed: Jul. 18, 2001

(86) PCT No.: PCT/US01/22517

§ 371 (c)(1),
(2), (4) Date: Jan. 8, 2004

(87) PCT Pub. No.: WO03/008428

PCT Pub. Date: Jan. 30, 2003

(65) Prior Publication Data

US 2004/0147414 A1    Jul. 29, 2004

(51) Int. Cl.
*C10M 141/10* (2006.01)

(52) U.S. Cl. .................................... 508/365; 508/110
(58) Field of Classification Search ................ 508/365
See application file for complete search history.

(56) References Cited

U.S. PATENT DOCUMENTS

| | | | |
|---|---|---|---|
| 3,336,219 A | 8/1967 | Glein | |
| 3,509,051 A | 4/1970 | Farmer et al. | |
| 4,098,705 A * | 7/1978 | Sakurai et al. | 508/363 |
| 4,683,316 A | 7/1987 | Singhal | |
| 5,605,880 A | 2/1997 | Arai et al. | |
| 5,688,748 A | 11/1997 | Tomizawa | |
| 5,786,307 A * | 7/1998 | Igarashi et al. | 508/365 |
| 6,187,722 B1 * | 2/2001 | Rowland et al. | 508/284 |
| 2002/0114980 A1 * | 8/2002 | Gunsel et al. | 428/695 |

OTHER PUBLICATIONS

Barrie, P., Coffey, T.A., Forster, G.D., Hogarth, G. J. Chem. Soc., Dalton Trans., 1999, 4519-4528.*

* cited by examiner

*Primary Examiner*—Vasu Jagannathan
*Assistant Examiner*—James Goloboy
(74) *Attorney, Agent, or Firm*—Daniel Reitenbach

(57) ABSTRACT

Organo-Imino molybdenum complexes are disclosed having the formula $Z_2N_2MOS_4C_2N_2R_4$ wherein Z and R are independently selected from the group consisting of linear hydrocarbon groups, branched hydrocarbon groups, cyclic hydrocarbon groups, and mixtures thereof. The compounds are useful as friction modifiers in lubricants.

21 Claims, No Drawings

ORGANO-IMIDO MOLYBDENUM COMPLEXES AS FRICTION MODIFIER ADDITIVES FOR LUBRICANT COMPOSITIONS

BACKGROUND OF THE INVENTION

1. Field of the Invention

It is well known that molybdenum compounds added to lubricating oils, depending on their structure, can play a significant role as both friction modifiers and as anti-wear additives. The present invention is related to lubricating oil additives and lubricant compositions, and more particularly to a novel class of molybdenum-based friction modifier additives derived from organo-imido molybdenum complexes that can be incorporated into lubricating oils. The purpose of the present invention is to provide additives that can reduce friction and aid formulators of engine oils to meet new requirements for passenger car motor oils, such as ILSAC GF-3.

2. Description of Related Art

Regulatory agencies today are seeking to improve the fuel economy of motor vehicles through legislation (CAFE requirements) that puts the responsibility for achieving such economy on the motor vehicle manufacturers, who in turn transfer at least a portion of this responsibility to lubricant oil manufacturers by means of engine oil specifications. As these fuel economy requirements become more and more rigorous, it becomes more and more important to incorporate friction modifier additives into lubricant compositions. It is well known that the fuel efficiency of engine oils can be improved by using friction reducing additives. It is also well understood that these additives must be active at engine operational temperature in order to be most effective.

In addition, zinc dialkyldithiophosphates (ZDDP) have been used in formulated oils as antiwear and antioxidant additives for more than 50 years. However, zinc dialkyldithiophosphates give rise to ash, which contributes to particulate matter in automotive exhaust emissions. Regulatory agencies are seeking to reduce emissions of zinc into the environment. Moreover, the phosphorus present in the dialkyldithiophosphates is also suspected of limiting the service life of catalytic converters that are used on vehicles to reduce pollution. It is important to limit the particulate matter and pollution formed during engine use for toxicological and environmental reasons, but it is also important to maintain undiminished the antiwear properties of the lubricating oil. In view of the aforementioned shortcomings with the known zinc- and phosphorus-containing additives, it is a further object of this invention to provide antiwear additives that contain neither zinc nor phosphorus.

In developing lubricating oils, there have been many attempts to provide additives that impart antifrictional or oiliness properties. Molybdenum compounds are known to be useful as friction modifiers and antioxidants and to be capable of providing antiwear and extreme pressure resistance properties in lubricating oil compositions.

Thiocarbamate additives for lubricating oils, particularly molybdenum-containing thiocarbamates, have been disclosed in the patent literature.

U.S. Pat. No. 3,419,589 discloses a process for the preparation of molybdenum (VI) dialkyldithiocarbamate complexes and sulfurized derivatives thereof in substantially high yields by the dilute nitric acid acidification of alkali dialkyldithiocarbamates and alkali molybdates and the subsequent treatment thereof with hydrogen sulfide to form the sulfurized derivatives of the reaction product. These compounds are said to be useful as additives for lubricants.

U.S. Pat. No. 3,509,051 discloses lubricating oils and greases that are said to exhibit excellent extreme pressure, antioxidant, and wear properties when they contain sulfurized oxymolybdenum dithiocarbamates of the general formula:

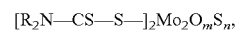

where m+n=4, m is in the range of 2.35 to 3, n is in the range of 1.65 to 1, and R is a hydrocarbon group having 1 to 24 carbon atoms.

U.S. Pat. No. 3,541,014 discloses lubricant compositions that are said to have improved extreme pressure capabilities and antiwear properties, which are characterized by the presence therein of oil-soluble molybdenum-containing organic complexes. These complexes are produced by contacting molybdenum-containing anions with oil-soluble overbased, Group II metal-containing compositions until a portion of the anions reacts with the Group II metal. Lubricating oils, cutting oils, greases, and the like are illustrative of the lubricant compositions disclosed.

U.S. Pat. No. 4,098,705 discloses a compound of the formula:

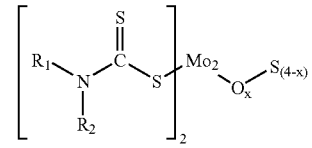

wherein $R_1$ and $R_2$ stand for a hydrocarbyl group having 1 to 24 carbon atoms and x is a number of 0.5-2.3 that is said to be useful as an additive for lubricants.

U.S. Pat. No. 4,164,473 discloses hydrocarbon-soluble organo molybdenum complexes obtained as the reaction product of a hydrocarbyl substituted hydroxy alkylated amine, e.g., N,N',N'-tris(2-hydroxy ethyl)-n-tallow-1,3-diaminopropane, with about one molar equivalent of a molybdenum compound, e.g., ammonium molybdate, that are said to be useful hydrocarbon additives particularly in combination with an oil-soluble sulfur donor, e.g., a metal dialkyl dithiophosphate to provide an additive combination for lubricating oils. Lubricating compositions comprising these coadditives are disclosed to exhibit improved antifriction and antiwear properties.

U.S. Pat. No. 4,259,194 discloses antioxidant additives for lubricating oil that are prepared by combining ammonium tetrathiomolybdate and a basic nitrogen compound complex to form a sulfur- and molybdenum-containing composition.

U.S. Pat. No. 4,259,195 discloses antioxidant additives for lubricating oil that are prepared by combining a polar promoter, an acidic molybdenum compound, and certain basic nitrogen compounds to form a molybdenum-containing composition.

U.S. Pat. No. 4,263,152 discloses the preparation of antioxidant additives for lubricating oil by combining water, an acidic molybdenum compound, a basic nitrogen compound complex and a sulfur source to form a sulfur- and molybdenum-containing composition.

U.S. Pat. No. 4,265,773 discloses antioxidant additives for lubricating oil that are prepared by combining an acidic molybdenum compound, an oil-soluble basic nitrogen compound, and carbon disulfide to form a sulfur- and molybdenum-containing composition.

U.S. Pat. No. 4,266,945 discloses the preparation of molybdenum-containing compositions by the reaction of an acid of molybdenum or a salt thereof, phenol or aldehyde condensation product therewith, and a primary or secondary amine. The preferred amines are diamines such as tallow-substituted trimethylene diamine and their formaldehyde condensation products. An optional but preferred ingredient in the reaction mixture is at least one oil-soluble dispersant. The molybdenum-containing compositions are said to be useful as additives in fuels and lubricants, especially so in lubricants when combined with compounds containing active sulfur.

U.S. Pat. No. 4,272,387 discloses antioxidant additives for lubricating oil that are prepared by combining an acidic molybdenum compound, a basic nitrogen compound complex, and a sulfur source to form a sulfur- and molybdenum-containing composition.

U.S. Pat. No. 4,283,295 discloses antioxidant additives for lubricating oil that are prepared by combining a polar promoter, ammonium tetrathiomolybdate, and a basic nitrogen compound complex to form a sulfur- and molybdenum-containing composition.

U.S. Pat. No. 4,285,822 discloses antioxidant additives for lubricating oil that are prepared by (1) combining a polar solvent, an acidic molybdenum compound, and an oil-soluble basic nitrogen compound to form a molybdenum-containing complex and (2) contacting said complex with carbon disulfide to form a sulfur- and molybdenum-containing composition.

U.S. Pat. No. 4,289,635 discloses molybdenum-containing compositions that are prepared by reacting an olefinically unsaturated compound capable of reacting with active sulfur with a composition prepared by reacting:

(a) a phosphorus-containing acid represented by the formula:

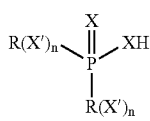

wherein each X and X' is independently oxygen or sulfur, each n is zero or one and each R is independently the same or a different hydrocarbon-based radical; and (b) at least one hexavalent molybdenum oxide compound, and (c) hydrogen sulfide, in the presence of (d) a polar solvent. It is said that the compositions are useful as additives for lubricants and that internal combustion engines exhibit improved fuel economy when lubricated with them.

U.S. Pat. No. 4,315,826 discloses multipurpose lubricant additives that are prepared by reaction of carbon disulfide with thiomolybdenum derivatives of polyalkenylsuccinimides having basic nitrogen functions. It is said that the subject additives function as dispersants possessing excellent antifriction properties and impart antiwear and antioxidant properties to a lubricant.

U.S. Pat. No. 4,369,119 discloses antioxidant additives for lubricating oil that are prepared by combining (a) a sulfur-containing molybdenum compound prepared by reacting an acidic molybdenum compound, a basic nitrogen compound, and a sulfur compound, with (b) an organic sulfur compound.

U.S. Pat. No. 4,370,246 discloses the preparation of an antioxidant additive combination for lubricating oils by combining (a) a sulfur containing molybdenum compound prepared by reacting an acidic molybdenum compound, a basic nitrogen compound, and a sulfur compound, with (b) an aromatic amine compound.

U.S. Pat. No. 4,395,343 discloses antioxidant additives for lubricating oil that are prepared by combining (a) a sulfur containing molybdenum compound prepared by reacting an acidic molybdenum compound, a basic nitrogen compound, and carbon disulfide, with (b) an organic sulfur compound.

U.S. Pat. No. 4,402,840 discloses antioxidant additives for lubricating oil that are prepared by combining (a) a sulfur containing molybdenum compound prepared by reacting an ammonium thiomolybdate compound, and a basic nitrogen compound, with (b) an organic sulfur compound.

U.S. Pat. No. 4,428,848 discloses compounds prepared by the reaction of an adduct of a phosphosulfurized polyisoalkylene or alpha olefin with an acidified hexavalent molybdenum salt which is said to give enhanced copper corrosion protection relative to the non-molybdenum treated adducts when incorporated in lubricants. Also disclosed is the combination of such compounds with a zinc dialkyldithiophosphate, which combination imparts to lubricants an oxidation inhibition that is said to be greater than is obtainable with either the zinc dialkyldithiophosphate or the molybdenum-containing adduct alone.

U.S. Pat. No. 4,474,673 discloses antifriction additives for lubricating oil that are prepared by reacting a sulfurized organic compound having an active hydrogen or potentially active hydrogen with a molybdenum halide.

U.S. Pat. No. 4,479,883 discloses a lubricating oil composition that is said to have particularly improved friction reducing properties that comprises an ester of a polycarboxylic acid with a glycol or glycerol and a selected metal dithiocarbamate and that contains a relatively low level of phosphorus.

U.S. Pat. No. 4,501,678 discloses a lubricant containing molybdenum dialkyldithiocarbamates that is said to be useful for improving the fatigue life of gears.

U.S. Pat. No. 4,765,918 discloses a lubricating oil additive prepared by reacting a triglyceride with a basic nitrogen compound to form a reaction product, reacting the reaction product with an acidic molybdenum compound to form an intermediate reaction product, and reacting the intermediate reaction product with a sulfur compound.

U.S. Pat. No. 4,889,647 discloses molybdenum complexes prepared by reacting (a) a fatty oil, (b) diethanolamine, and (c) a molybdenum source. The complexes are said to impart antifriction and antiwear properties to lubricating compositions and to decrease fuel consumption in internal combustion engines.

U.S. Pat. No. 4,995,996 discloses a lubricating composition comprising a major amount of an oil of lubricating viscosity and a minor amount of an additive having the formula $Mo_2L_4$ wherein L is a ligand selected from xanthates and mixtures thereof and, in particular, xanthates having a sufficient number of carbon atoms to render the additive soluble in the oil. In general, the xanthate ligand, L, will have about 2 to 30 carbon atoms.

U.S. Pat. No. 5,605,880 discloses a lubricating oil composition which is obtained by containing in (A) a base oil in which the content of the aromatic ingredients is 3.0% by weight or less, N is 50 ppm by weight or less, S is 50 ppm by weight, and the viscosity is 2.0-50.0 mm²/s, based on the total weight of the composition, (3) 0.05-2.0% by weight of alkyldiphenylamine(s) and/or phenyl-α-naphthylamine(s) and (C) MoDTC of $C_{8-23}$ and/or $C_{3-18}$ in an amount of 50-2,000 ppm by weight in terms of the amount of molybdenum. Such a lubricating oil composition is said to have high heat-resistant properties, a high stability to oxidation, and improved friction characteristics, and is suitably used especially as a lubricating oil for internal combustion engines.

U.S. Pat. No. 5,650,381 discloses a lubricating oil composition which contains from about 100 to 450 parts per million of molybdenum from a molybdenum compound which is substantially free of active sulfur and about 750 to 5,000 parts per million of a secondary diarylamine. This combination of ingredients is said to provide improved oxidation control and friction modifier performance to the lubricating oil. The composition is particularly suited for use as a crankcase lubricant. (See, also, U.K. 2,307,245.)

U.S. Pat. No. 5,688,748 discloses a lubricating oil composition for internal combustion engines which is said to have high resistance to oxidation by nitrogen oxides, excellent friction characteristics that is maintained for a prolonged period, and the ability to reduce the fuel consumption for a prolonged period. The lubricating oil composition consists of a base oil principally consisting of a hydrocarbon oil which has a dynamic viscosity of 2-20 mm²/s at 100° C. and contains 3 wt % or less aromatic components in total, 45 wt % or more one- and two-ring naphthenes in total, 50 wt ppm or less sulfur and 50 wt ppm or less nitrogen, to which are added, with respect to the total weight of the composition, 0.02-0.2 wt % as molybdenum of molybdenum dithiocarbamate, 0.02-0.15 wt % as phosphorus of zinc dithiophosphate, and 0.05-3 wt % of phenol-based antioxidant. The lubricating oil composition is said to have a low friction coefficient, which is maintained for a prolonged period even after oxidation by nitrogen oxides.

U.S. Pat. No. 5,840,672 discloses antioxidant compositions comprising (A) at least one secondary diarylamine, (B) at least one sulfurized olefin and/or sulfurized hindered phenol, and (C) at least one oil soluble molybdenum compound. These antioxidant compositions are said to be highly effective at providing oxidative stability to lubricating compositions, especially for highly saturated, low sulfur lubrication base oils.

U.S. Pat. No. 6,103,674 discloses a lubricating oil additive that comprises the reaction product of:

(a) an unsaturated or saturated ester or acid,
(b) a diamine of the formula:

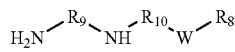

(c) carbon disulfide, and
(d) a molybdenum compound, wherein $R_8$ is an alkyl group of 1 to 40 carbon atoms, $R_9$ and $R_{10}$ are independently selected aliphatic or aromatic moieties, W is oxygen, sulfur, or —CH₂—. The additive imparts friction modification and beneficial antiwear, extreme pressure, and oxidation stability properties to the lubricating oil.

U.S. Pat. No. 6,117,826 discloses dithiocarbamyl derivatives that are useful as multifunctional additives for lubricating oils.

EP 719313 B1 broadly claims molybdenum dialkylthiocarbamates ($C_{7-24}$) and alkylated diphenylamines in lubricating oils.

The disclosures of the foregoing references are incorporated herein by reference in their entirety.

SUMMARY OF THE INVENTION

The present invention provides a lubricating oil organoimido molybdenum complex additive that imparts friction modification properties to a lubricant.

More particularly, the present invention is directed to a composition of matter comprising a compound of the formula

wherein Z and R are independently selected from the group consisting of linear hydrocarbon groups, branched hydrocarbon groups, cyclic hydrocarbon groups, and mixtures thereof.

In another embodiment, the present invention is directed to a lubricant additive comprising a compound of the formula

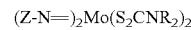

wherein Z and R are independently selected from the group consisting of linear hydrocarbon groups, branched hydrocarbon groups, cyclic hydrocarbon groups, and mixtures thereof.

In still another embodiment, the present invention is directed to a method for reducing the coefficient of friction of a lubricant comprising adding to said lubricant a compound of the formula

wherein Z and R are independently selected from the group consisting of linear hydrocarbon groups, branched hydrocarbon groups, cyclic hydrocarbon groups, and mixtures thereof.

DESCRIPTION OF THE PREFERRED EMBODIMENTS

As disclosed above, the present invention is directed to a composition of matter that is useful as a friction-modifying additive to lubricants, especially lubricating oils. The composition is a compound of the formula

wherein Z and R are independently selected from the group consisting of linear hydrocarbon groups, branched hydrocarbon groups, cyclic hydrocarbon groups, and mixtures thereof.

Preferably, the hydrocarbon groups referred to have from 1 to about 44 carbon atoms, more preferably from 1 to about 22 carbon atoms. The hydrocarbon groups can be fully saturated or partially unsaturated and can have either a straight chain or a branched chain or they can be cyclic. Thus, R and Z can, for example, independently be methyl, ethyl, propyl, butyl, tert-butyl, pentyl, hexyl, 2-ethyl hexyl, heptyl, octyl, isooctyl, tert-octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, triacontyl, pentatriacontyl, tetracontyl, cyclopropyl, cyclobutyl, cyclopentyl, cyclohexyl, and the like, and isomers and mixtures thereof.

Additionally, contained within the chains of R and/or Z may be ester groups or heteroatoms, such as oxygen and sulfur, which may take the form of ethers, polyethers, and/or sulfides.

The additives of the present invention can be synthesized by the following scheme:

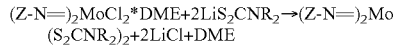

(Z-N=)$_2$MoCl$_2$*DME+2LiS$_2$CNR$_2$→(Z-N=)$_2$Mo(S$_2$CNR$_2$)$_2$+2LiCl+DME wherein Z and R are independently selected from the group consisting of linear hydrocarbon groups, branched hydrocarbon groups, cyclic hydrocarbon groups, and mixtures thereof.

The starting material, (Z-N=)$_2$MoCl$_2$*DME, can be made by the reaction of linear and/or branched alkylamines with Na$_2$MoO$_4$+DME (dimethoxyethane)+trimethylsilylchloride.

LiS$_2$CNR$_2$ can be made by reacting butyl lithium with a secondary amine, followed by reaction with carbon disulfide. For example,

LiBu+HNR$_2$→LiNR$_2$

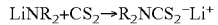

LiNR$_2$+CS$_2$→R$_2$NCS$_2^-$Li$^+$

The additives of this invention can be used with or without other friction modifiers as either a partial or complete replacement for those currently used. They can also be used in combination with other additives typically found in motor oils, as well as other ashless anti-wear additives and other antioxidants. Typical additives found in lubricating oils are dispersants, detergents, corrosion/rust inhibitors, antioxidants, e.g., secondary amine antioxidants, hindered phenolic antioxidants, sulfur-containing hindered phenolic antioxidants, sulfurized olefins, thiadiazoles, metal deactivators, antiwear agents, e.g., zinc dialkyldithiophosphates, antifoamants, friction modifiers, seal swell agents, demulsifiers, VI improvers, and pour point depressants. See, for example, U.S. Pat. No. 5,498,809, incorporated herein by reference, for a description of useful lubricating oil composition additives.

Examples of dispersants include polyisobutylene succinimides, polyisobutylene succinate esters, Mannich Base ashless dispersants, and the like. Examples of detergents include metallic phenates, metallic sulfonates, metallic salicylates, metallic calexranes, and the like. Examples of friction modifiers that can be used in combination with the friction modifiers of the present invention include fatty acid esters and amides, glycerol mono oleate, organo molybdenum compounds, molybdenum dialkyldithiocarbamates, molybdenum dialkyl dithiophosphates, and the like. An example of an antifoamant is polysiloxane, and the like. An example of a rust inhibitor is polyoxyalkylene polyols, and the like. Examples of VI improvers include olefin copolymers and dispersant olefin copolymers, and the like. An example of a pour point depressant is poly(methyl methacrylate), and the like.

Examples of antioxidant additives that can be used in combination with the additives of the present invention include alkylated diphenylamines and N-alkylated phenylenediamines. Secondary diarylamines are well known antioxidants and there is no particular restriction on the type of secondary diarylamine that can be used in the practice of the present invention. The secondary diarylamine type of antioxidant in a lubricating oil provides a synergistic antioxidant mixture with the additive of the present invention. Preferably, the secondary diarylamine antioxidant is of the general formula R$_{11}$—NH—R$_{12}$, where R$_{11}$ and R$_{12}$ each independently represent a substituted or unsubstituted aryl group having 6 to 46 carbon atoms. Illustrative of substituents for the aryl group are aliphatic hydrocarbon groups such as alkyl having 1 to 40 carbon atoms, hydroxyl, carboxyl, amino, N-alkylated amino, N',N-dialkylated amino, nitro, or cyano. The aryl is preferably substituted or unsubstituted phenyl or naphthyl, particularly where one or both of the aryl groups are substituted with alkyl such as one having 4 to 24 carbon atoms. Preferred alkylated diphenylamines that can be employed in the practice of the present invention include nonylated diphenylamine, octylated diphenylamine (e.g., di(octylphenyl)amine), styrenated diphenylamine, octylated styrenated diphenylamine, and butylated octylated diphenylamine.

The alkyl moiety of 1 to 40 carbon atoms can have either a straight or a branched chain, which can be either a fully saturated or a partially unsaturated hydrocarbon chain, e.g., methyl, ethyl, propyl, butyl, pentyl, hexyl, 2-ethyl hexyl, heptyl, octyl, nonyl, decyl, undecyl, dodecyl, tridecyl, tetradecyl, pentadecyl, hexadecyl, heptadecyl, octadecyl, oleyl, nonadecyl, eicosyl, heneicosyl, docosyl, tricosyl, tetracosyl, pentacosyl, tricontyl, pentatriacontyl, tetracontyl, and the like, and isomers and mixtures thereof.

Examples of some secondary diarylamines that can be employed in the practice of the present invention include: diphenylamine, dialkylated diphenylamine, trialkylated diphenylamine, or mixtures thereof, 3-hydroxydiphenylamine, 4-hydroxydiphenylamine, N-phenyl-1,2-phenylenediamine, N-phenyl-1,4-phenylenediamine, mono- and/or dibutyldiphenylamine, mono- and/or di-octyldiphenylamine, mono- and/or di-nonyldiphenylamine, phenyl-α-naphthylamine, phenyl-β-naphthylamine, di-heptyldiphenylamine, mono- and/or di-(α-methylstyryl)diphenylamine, mono- and/or di-styryldiphenylamine, N,N'-diisopropyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-diphenyl-p-phenylenediamine, N,N'-di-(naphthyl-2)-p-phenylenediamine, N-isopropyl-N'-phenyl-p-phenylenediamine, N-(1,3-dimethylbutyl)-N'-phenyl-p-phenylenediamine, N-(1-methylpentyl)-N'-phenyl-p-phenylenediamine, N-cyclohexyl-N'-phenyl-p-phenylenediamine, 4-(p-toluenesulfonamido)diphenylamine, 4-isopropoxydiphenylamine, tert-octylated N-phenyl-1-naphthylamino, and mixtures of mono- and dialkylated t-butyl-t-octyldiphenylamines.

Another example of the antioxidant types that can be used in combination with the additives of the present invention is the hindered phenolic type. As illustrative of oil soluble phenolic compounds, may be listed alkylated monophenols, alkylated hydroquinones, hydroxylated thiodiphenyl ethers, alkylidenebis phenols, benzyl compounds, acylaminophenols, and esters and amides of hindered phenol-substituted alkanoic acids. In a preferred embodiment of the present invention, 3,5-di-t-butyl-4-hydroxy-hydrocinnamic acid, a C$_7$-C$_9$ branched alkylester of 2,6-di-t-butyl-p-cresol, and mixtures thereof are included in the lubricant compositions.

Another example of an antioxidant type that can be used in combination with the additives of the present invention are oil soluble copper compounds, and the like.

Examples of antiwear additives that can be used in combination with the additives of the present invention include organo borates, organo phosphites, organic sulfur-containing compounds, zinc dialkyl dithiophosphates, zinc diaryl dithiophosphates, phosphosulfurized hydrocarbon, and the like.

Suitable phosphates for use as antiwear agents include dihydrocarbyl dithiophosphates, wherein the hydrocarbyl groups contain an average of at least three carbon atoms. Particularly useful are metal salts of at least one dihydrocarbyl dithiophosphoric acid wherein the hydrocarbyl groups contain an average of at least three carbon atoms. The acids from which the dihydrocarbyl dithiophosphates can be derived can be illustrated by acids of the formula

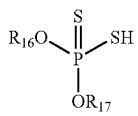

wherein $R_{16}$ and $R_{17}$ are the same or different and are alkyl, cycloalkyl, aralkyl, alkaryl, or substituted substantially hydrocarbon radical derivatives or any of the above groups and wherein the $R_{16}$ and $R_{17}$ groups in the acid each have on average at least three carbon atoms. By "substantially hydrocarbon" is meant radicals containing substituent groups (e.g., one to four substituent groups per radical moiety) such as ether, ester, nitro, or halogen that do not materially affect the hydrocarbon character of the radical.

Specific examples of suitable $R_{16}$ and $R_{17}$ radicals include isopropyl, isobutyl, n-butyl, sec-butyl, n-hexyl, heptyl, 2-ethyl hexyl, diisobutyl, isooctyl, decyl, dodecyl, tetradecyl, hexadecyl, octadecyl, butylphenyl, o,p-dipentylphenyl, octylphenyl, polyisobutene-(molecular weight 350)-substituted phenyl, tetrapropylene-substituted phenyl, β-octylbutylnaphthyl, cyclopentyl, cyclohexyl, phenyl, chlorophenyl, o-dichlorophenyl, bromophenyl, naphthenyl, 2-methylcyclohexyl, benzyl, chlorobenzyl, chloropentyl, dichlorophenyl, nitrophenyl, dichlorodecyl, xenyl radicals, and the like. Alkyl radicals having from about 3 to about 30 carbon atoms and aryl radicals having about 6 to about 30 carbon atoms are preferred. Particularly preferred $R_{16}$ and $R_{17}$ radicals are alkyl of 4 to 18 carbon atoms.

The phosphorodithioic acids are readily obtainable by the reaction of phosphorus pentasulfide and an alcohol or phenol. The reaction involves mixing, at a temperature of about 20° C. to about 200° C., four moles of the alcohol or phenol with one mole of phosphorus pentasulfide. Hydrogen sulfide is liberated as the reaction takes place. Mixtures of alcohols, phenols, or both can be employed, e.g., mixtures of $C_3$ to $C_{30}$ alcohols, $C_6$ to $C_{30}$ aromatic alcohols, etc.

The metals useful to make the phosphate salts include Group I metals, Group II metals, aluminum, lead, tin, molybdenum, manganese, cobalt, and nickel. Zinc is the preferred metal. Examples of metal compounds that can be reacted with the acid include lithium oxide, lithium hydroxide, lithium carbonate, lithium pentylate, sodium oxide, sodium hydroxide, sodium carbonate, sodium methylate, sodium propylate, sodium phenoxide, potassium oxide, potassium hydroxide, potassium carbonate, potassium methylate, silver oxide, silver carbonate, magnesium oxide, magnesium hydroxide, magnesium carbonate, magnesium ethylate, magnesium propylate, magnesium phenoxide, calcium oxide, calcium hydroxide, calcium carbonate, calcium methylate, calcium propylate, calcium pentylate, zinc oxide, zinc hydroxide, zinc carbonate, zinc propylate, strontium oxide, strontium hydroxide, cadmium oxide, cadmium hydroxide, cadmium carbonate, cadmium ethylate, barium oxide, barium hydroxide, barium hydrate, barium carbonate, barium ethylate, barium pentylate, aluminum oxide, aluminum prolylate, lead oxide, lead hydroxide, lead carbonate, tin oxide, tin butylate, cobalt oxide, cobalt hydroxide, cobalt carbonate, cobalt pentylate, nickel oxide, nickel hydroxide, nickel carbonate, and the like.

In some instances, the incorporation of certain ingredients, particularly carboxylic acids or metal carboxylates such as small amounts of the metal acetate or acetic acid used in conjunction with the metal reactant will facilitate the reaction and result in an improved product. For example, the use of up to about five percent of zinc acetate in combination with the required amount of zinc oxide facilitates the formation of a zinc phosphorodithioate.

The preparation of metal phosphorodithioates is well known in the art and is described in a large number of issued patents, including U.S. Pat. Nos. 3,293,181, 3,397,145, 3,396,109, and 3,442,804, the disclosures of which are incorporated herein by reference in their entirety.

Also useful as antiwear additives are amine derivatives of dithiophosphoric acid compounds such as are described in U.S. Pat. No. 3,637,499, the disclosure of which is incorporated herein by reference in its entirety.

The zinc salts are most commonly used as antiwear additives in lubricant oil in amounts of 0.1 to 10, preferably 0.2 to 2, weight percent, based upon the total weight of the lubricating oil composition. They may be prepared in accordance with known techniques by first forming a dithiophosphoric acid, usually by reaction of an alcohol or a phenol with $P_2S_5$, and then neutralizing the dithiophosphoric acid with a suitable zinc compound.

Mixtures of alcohols may be used including mixtures of primary and secondary alcohols, secondary generally for imparting improved antiwear properties, and primary for thermal stability. Mixtures of the two are particularly useful. In general, any basic or neutral zinc compound could be used, but the oxides, hydroxides, and carbonates are most generally employed. Commercial additives frequently contain an excess of zinc owing to the use of an excess of basic zinc compound in the neutralization reaction.

The zinc dihydrocarbyl dithiophosphates (ZDDP) are oil soluble salts of dihydrocarbyl esters of dithiophosphoric acids and may be represented by the following formula

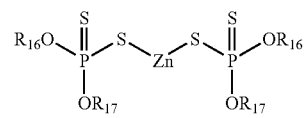

wherein $R_{16}$ and $R_{17}$ are as described in connection with the previous formula.

Where additional additives are employed in the practice of the present invention, it is especially preferred that they be selected from the group consisting of zinc dialkyldithiophosphates, zinc diaryldithiophosphates, alkylated diphenylamines, hindered alkylated phenolics, and mixtures thereof.

Compositions, when containing these additives, typically are blended into the base oil in amounts that are effective to provide their normal attendant function. Representative effective amounts of such additives are illustrated as follows:

| Compositions | Broad Weight % | Preferred Weight % |
| --- | --- | --- |
| V.I. Improver | 1–12 | 1–4 |
| Corrosion Inhibitor | 0.01–3 | 0.01–1.5 |
| Oxidation Inhibitor | 0.01–5 | 0.01–1.5 |

-continued

| Compositions | Broad Weight % | Preferred Weight % |
|---|---|---|
| Dispersant | 0.1–10 | 0.1–5 |
| Lube Oil Flow Improver | 0.01–2 | 0.01–1.5 |
| Detergents/Rust Inhibitors | 0.01–6 | 0.01–3 |
| Pour Point Depressant | 0.01–1.5 | 0.01–0.5 |
| Antifoaming Agents | 0.001–0.1 | 0.001–0.01 |
| Antiwear Agents | 0.001–5 | 0.001–1.5 |
| Seal Swellant | 0.1–8 | 0.1–4 |
| Friction Modifiers | 0.01–3 | 0.01–1.5 |
| Lubricating Base Oil | Balance | Balance |

When other additives are employed, it may be desirable, although not necessary, to prepare additive concentrates comprising concentrated solutions or dispersions of the subject additives of this invention (in concentrate amounts hereinabove described), together with one or more of the other additives (the concentrate when constituting an additive mixture being referred to herein as an additive-package) whereby several additives can be added simultaneously to the base oil to form the lubricating oil composition. Dissolution of the additive concentrate into the lubricating oil can be facilitated by solvents and by mixing accompanied by mild heating, but this is not essential. The concentrate or additive-package will typically be formulated to contain the additives in proper amounts to provide the desired concentration in the final formulation when the additive-package is combined with a predetermined amount of base lubricant. Thus, the subject additives of the present invention can be added to small amounts of base oil or other compatible solvents along with other desirable additives to form additive-packages containing active ingredients in collective amounts of typically about 2.5 to about 90 percent, and preferably about 15 to about 75 percent, and most preferably about 25 to about 60 percent by weight additives in the appropriate proportions with the remainder being base oil. The final formulations can employ typically about 1 to 20 weight percent of the additive-package with the remainder being base oil.

All of the weight percentages expressed herein (unless otherwise indicated) are based on active ingredient (AI) content of the additive and/or upon the total weight of any additive-package or formulation, which will be the sum of the AI weight of each additive plus the weight of total oil or diluent.

In general, the lubricant compositions of the present invention contain the additives in a concentration ranging from about 0.05 to about 30 weight percent. A concentration range for the additives ranging from about 0.1 to about 10 weight percent based on the total weight of the oil composition is preferred. A preferred concentration range is from about 0.2 to about 5 weight percent. Oil concentrates of the additives can contain about 1 to about 75 weight percent of the additive reaction product in a carrier or diluent oil of lubricating oil viscosity.

In general, the additives of the present invention are useful in a variety of lubricating oil basestocks. The lubricating oil basestock is any natural or synthetic lubricating base oil stock fraction having a kinematic viscosity at 100° C. of about 2 to about 200 cSt, more preferably about 3 to about 150 cSt, most preferably about 3 to about 100 cSt. The lubricating oil basestock can be derived from natural lubricating oils, synthetic lubricating oils, or mixtures thereof. Suitable lubricating oil basestocks include basestocks obtained by isomerization of synthetic wax and wax, as well as hydrocrackate basestocks produced by hydrocracking (rather than solvent extracting) the aromatic and polar components of the crude. Natural lubricating oils include animal oils, vegetable oils (e.g., rapeseed oils, castor oils, and lard oil), petroleum oils, mineral oils, and oils derived from coal or shale.

Synthetic oils include hydrocarbon oils and halo-substituted hydrocarbon oils, such as polymerized and interpolymerized olefins, alkylbenzenes, polyphenyls, alkylated diphenyl ethers, alkylated diphenyl sulfides as well as their derivatives, analogs, and homologs, and the like. Synthetic lubricating oils also include alkylene oxide polymers, interpolymers, copolymers, and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from $C_5$ to $C_{12}$ monocarboxylic acids and polyols and polyol ethers.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The lubricating oil can be derived from unrefined, refined, rerefined oils, or mixtures thereof. Unrefined oils are obtained directly from a natural source or synthetic source (e.g., coal shale, or tar and bitumen) without further purification or treatment. Examples of unrefined oils include a shale oil obtained directly from a retorting operation, a petroleum oil obtained directly from distillation, or an ester oil obtained directly from an esterification process, each of which is then used without further treatment. Refined oils are similar to the unrefined oils except that refined oils have been treated in one or more purification steps to improve one or more properties. Suitable purification techniques include distillation, hydrotreating, dewaxing, solvent extraction, acid or base extraction, filtration, and percolation, all of which are known to those skilled in the art. Rerefined oils are obtained by treating refined oils in processes similar to those used to obtain the refined oils. These rerefined oils are also known as reclaimed or reprocessed oils and often are additionally processed by techniques for removal of spent additives and oil breakdown products.

Lubricating oil base stocks derived from the hydroisomerization of wax can also be used, either alone or in combination with the aforesaid natural and/or synthetic base stocks. Such wax isomerate oil is produced by the hydroisomerization of natural or synthetic waxes or mixtures thereof over a hydroisomerization catalyst. Natural waxes are typically the slack waxes recovered by the solvent dewaxing of mineral oils; synthetic waxes are typically the wax produced by the Fisher-Tropsch process. The resulting isomerate product is typically subjected to solvent dewaxing and fractionation to recover various fractions of specific viscosity range. Wax isomerate is also characterized by processing very high viscosity indices, generally having a VI of at least 130, preferably at least 135 and higher, and, following dewaxing, a pour point of about −20° C. and higher.

The additives of the present invention are especially useful as components in many different lubricating oil compositions. The additives can be included in a variety of oils with lubricating viscosity, including natural and synthetic lubricating oils and mixtures thereof. The additives can be included in crankcase lubricating oils for spark-ignited and compression-ignited internal combustion engines. The compositions can also be used in gas engine lubricants, turbine lubricants, automatic transmission fluids, gear lubricants, compressor lubricants, metal-working lubricants, hydraulic fluids, and other lubricating oil and grease compositions. The additives can also be used in motor fuel compositions.

The advantages and the important features of the present invention will be more apparent from the following examples.

EXAMPLE 1

Bis-tert-butylimidomolybdenum(VI) dichloride, DME adduct

All operations with molybdenum derivatives were carried out in an atmosphere of dry argon. Anhydrous $Na_2MoO_4$ (30.9 g, 0.15 mol), absolutized DME (0.5 L), triethylanine (84 mL, 0.6 mol), trimethylsilylchloride (152 mL, 1.2 mol), and tert-butylamine (31.3 mL, 0.3 mol) were mixed in a 1 L flask, and refluxed for 12 hours. The $Na_2MoO_4$ was completely dissolved. The reaction mixture was filtered and the solid ($Et_3HN^+Cl^-$) was washed twice with DME and once with hot heptane. The solvents were removed in vacuo from the combined liquid phases, and the greenish solid mass obtained was vigorously shaken with cold hexane. The hexane was filtered off to yield 42.5 g (70%) of yellow crystals.

EXAMPLE 2

Bis-tert-octylimidomolybdenum(VI) dichloride, DME adduct

All operations with molybdenum derivatives were carried out in an atmosphere of dry argon. $MoO_2Cl_2 \cdot DME$ (18 g, 0.0625 mol), tert-octylamine (20.1 mL, 0.125 mol), triethylamine (35 mL, 0.25 mol), trimethylsilylchloride (31.6 mL, 0.25 mol), and DME (200 mL) were mixed together and refluxed for 5 hours. After cooling the solution to room temperature, the precipitate was filtered off, the solution was evaporated under diminished pressure to ¼ of its initial volume, and the filtration was repeated. Then, the remaining solvents were removed in vacuo, providing a red oily product, which was recrystallized twice from pentane at −110° C. A red crystalline solid was obtained. The yield was 23 g (72%).

EXAMPLE 3

Bis-(tert-butylimido)-bis-(diisooctyldithiocarbamato) molybdenum (VI)

$C_{42}H_{86}MoN_4S_4$

All operations with molybdenum derivatives were carried out in an atmosphere of dry argon. To a solution of bis-(iso-octyl)amine (10.6 mL, 0.0351 mol) in diethyl ether (200 mL) at 0° C., a 1.48 M solution of butyllithium in hexane (24 mL, 0.0351 mol) was carefully added with stirring. After stirring the mixture for 10 minutes, $CS_2$ (2.1 mL, 0.0351 mol) was carefully added, and the temperature allowed to rise to 20° C. Then, a solution of 7 g of Example 1 Product (0.0175 mol) in 50 mL DME was added, and after stirring for two hours, the solvents were evaporated under reduced pressure to a volume of 50 mL, One hundred mL of n-hexane was added, and the solution was filtered. The filtrate was evaporated in vacuo, and 15.5 g of a dark-red oil was obtained.

EXAMPLE 4

Bis-(tert-octylimido)-bis-(diisooctyldithiocarbamato) molybdenum (VI)

$C_{50}H_{102}MoN_4S_4$

All operations with molybdenum derivatives were carried out in an atmosphere of dry argon. To a solution of bis-(iso-octyl)amine (4.1 mL, 0.0137 mol) in 100 mL of diethyl ether at 0° C., a 1.48 M solution of butyllithium in hexane (9.3 mL, 0.0137 mol) was carefully added with stirring. After stirring the mixture for 10 minutes, $CS_2$ (0.83 mL, 0.0137 mol) was carefully added, and the temperature was allowed to rise to 20° C. Then, a solution of 3.5 g of Example 2 Product (0.00686 mol) in 30 mL DME was added, and after stirring for 10 minutes, the solvents were evaporated under reduced pressure to a volume of 30 mL. Seventy mL of n-hexane was added, and the solution was filtered. The filtrate was evaporated in vacuo, and 7.2 g of a dark-red oil was obtained.

EXAMPLE 5

$(tert-octylN)_2Mo\{S_2CN(Coco)_2\}_2$

All operations with molybdenum derivatives were carried out in an atmosphere of dry argon. To a solution of 10 g of dicocoamine in 200 mL of diethyl ether at 0° C., a 1.58 M solution of butyllithium in hexane (15.3 mL, 0.0242 mol) was carefully added with stirring. After stirring the mixture for 15 minutes, 1.46 mL of $CS_2$ (0.0242 mol) was carefully added, and the temperature was allowed to rise to 20° C. Then a solution of 6.18 g (0.0121 mol) of Example 2 Product in 20.9 mL DME was added, and after stirring for two hours, the solvents were evaporated under reduced pressure to a volume of 50 mL. One hundred mL of n-hexane was added, and the solution was filtered. The filtrate was evaporated in vacuo, and 16.8 g of a dark-red oil was obtained.

EXAMPLE 6

$(tert-butylN)_2Mo\{S_2CN(Coco)_2\}_2$

All operations with molybdenum derivatives were carried out in an atmosphere of dry argon. To a solution of 10 g of dicocoamine in 200 mL of diethyl ether at 0° C., a 1.58 M solution of butyrithium in hexane (15.3 mL, 0.0242 mol) was carefully added with stirring. After stirring the mixture for 15 minutes, 1.46 mL of $CS_2$ (0.0242 mol) was carefully added, and the temperature was allowed to rise to 20° C. Then, a 0.324 M solution of Example 1 Product in DME (37.3 mL, 0.0121 mol) was added, and after stirring for 20 minutes, the solvents were evaporated under reduced pressure to a volume of 50 mL. One hundred mL of n-hexane was added, and the solution was filtered. The filtrate was evaporated in vacuo, and 13.6 g of a dark-red oil was obtained.

EXAMPLE 7

Cameron-Plint TE77 High Frequency Friction Machine Friction Coefficient Testing

The anti-friction properties of the novel reaction product in a fully formulated lubricating oil were determined in the Cameron Plint TE77 Friction Test. The fully formulated lubricating oils tested contained 1 wt. % of the additive to be tested. The additives were tested for effectiveness in a motor oil at increasing temperature points and compared to identical formulations with and without the friction. In Table 1, the numerical value of the test results (Coefficient of Friction) decreases with an increase in effectiveness. In other words, the lower the Friction Coefficient value the better the additive is at reducing friction.

The test procedure for determining the friction coefficient with the Cameron-Plint TE77 High Frequency Friction Machine is as follows. Ten mL of an oil sample containing additive is placed in the test chamber so as to cover a flat stationary hardened ground NSOH B01 Gauge Plate (RC 60/0.4 micron). A reciprocating specimen, a 16 mm long nitrided steel dowel pin (6 mm diameter, 60 Rc), is placed on top of the steel plate under 50 Newton load, allowed to heat up to 35° C. from room temperature over 10 minutes and maintained at 35° C. for 5 minutes. Then, with the 50 Newton load in place, the reciprocation frequency of 5 Hertz is begun with a 15 millimeter amplitude stroke length. The temperature is then ramped up to 50° C. over 10 minutes and maintained at 50° C. for 5 minutes. The load is then increased to 100 Newtons and the temperature is ramped up to 165° C. over 1 hour. Friction Coefficient data are collected between 60-160° C. The flat specimen is cleaned between runs with hexanes and #500 emery cloth. A new dowel pin or surface of the dowel pin is used each time. A reference oil is run alternately between experimental oils. The same flat specimen is used until the reference oil no longer provides reproducible results.

The motor oil formulation tested is a SAE 10W-30 grade containing dispersant, detergent, antioxidant, rust inhibitor, pour point depressant, OCP VI Improver, and anti-wear additive. Friction modifier was added as a top treat to this formula.

TABLE 1

Cameron-Plint High Frequency Friction Machine Friction Results

| Blend ID | Additive | Weight % | C of F (μ) @ 60° C. | C of F (μ) @ 120° C. | C of F (μ) @ 160° C. |
|---|---|---|---|---|---|
| 392-014 | Example 3 | 1.0 | 0.037 | 0.042 | 0.035 |
| 392-020 | Example 4 | 1.0 | 0.095 | 0.038 | 0.035 |
| 392-086 | Example 5 | 1.0 | 0.057 | 0.033 | 0.027 |
| 392-089 | Example 6 | 1.0 | 0.075 | 0.037 | 0.033 |
| No FM[1] | — | 0.0 | 0.125 | 0.120 | 0.100 |
| CFM[2] | — | 1.0 | 0.115 | 0.115 | 0.121 |

[1]The reference oil is a fully formulated 10W-30 gasoline crank case motor oil containing no friction modifier.
[2]CFM is an ashless commercially available friction modifier based upon a mixture of fatty acid amides, glycerol esters, and glycerol.

EXAMPLE 8

Four-Ball Anti-Wear Testing

The anti-wear properties of the novel reaction product in a fully formulated lubricating oil were determined in the Four-Ball Wear Test under the ASTM D 4172 test conditions. The fully formulated lubricating oils tested also contained 1 wt. % cumene hydroperoxide to help simulate the environment within a running engine. The additives were tested for effectiveness in two motor oil formulations (see Table 2) and compared to identical formulations with and without any zinc dialkyldithiophosphate. In Table 3 the numerical value of the test results (Average Wear Scar Diameter, mm) decreases with an increase in effectiveness.

TABLE 2

SAE 10W-30 Motor Oil Formulations

| Formulation A | wt. % | Formulation B | wt. % |
|---|---|---|---|
| Solvent Neutral 100 | Balance | Solvent Neutral 100 | Balance |
| Solvent Neutral 150 | 60 | Solvent Neutral 150 | 60 |
| Succinimide Dispersant | 7.5 | Succinimide Dispersant | 7.5 |
| Overbased Calcium Phenate Detergent | 2.0 | Overbased Calcium Sulfonate Detergent | 2.0 |
| Neutral Calcium Sulfonate Detergent | 0.5 | Neutral Calcium Sulfonate Detergent | 0.5 |
| Antioxidant | 0.5 | Antioxidant | 0.5 |
| Rust Inhibitor | 0.1 | Rust Inhibitor | 0.1 |
| Pour Point Depressant | 0.1 | Pour Point Depressant | 0.1 |
| OCP VI Improver | 5.5 | OCP VI Improver | 5.5 |
| Antiwear Additive[1] | 1.0 | Antiwear Additive | 1.0 |

[1]In the case of No antiwear additive in Table 3, solvent neutral 100 is put in its place at 1.0 weight percent. The formulation is treated so that 1 weight percent anti-wear additive is based upon 100 percent active material.

TABLE 3

Falex Four-Ball Wear Results

| Compound | Formulation | Wear Scar Diameter, mm |
|---|---|---|
| No anti-wear additive | A | 0.93 |
| Zinc dialkyldithiophosphate | A | 0.46 |
| Example 5 | A | 0.56 |
| Example 6 | A | 0.85 |
| No anti-wear additive | B | 0.98 |
| Zinc dialkyldithiophosphate | B | 0.53 |
| Example 3 | B | 0.44 |
| Example 4 | B | 0.78 |
| Example 5 | B | 0.44 |
| Example 6 | B | 0.70 |

In view of the many changes and modifications that can be made without departing from principles underlying the invention, reference should be made to the appended claims for an understanding of the scope of the protection to be afforded the invention.

What is claimed is:

1. A composition of matter comprising a compound selected from the group consisting of bis-(tert-butylimido)-bis-diisooctyldithiocarbamato)-molybdenum (VI), bis-(tert-octylimido)-bis-diisooctyldithiocarbamato)-molybdenum (VI), (tert-octylN)$_2$Mo$\{S_2CN(Coco)_2\}_2$, and (tert-butylN)$_2$Mo$\{S_2CN(Coco)_2\}_2$.

2. The composition of claim 1 wherein the compound is bis-(tert-butylimido)-bis-diisooctyldithiocarbamato)-molybdenum (VI).

3. The composition of claim 1 wherein the compound is bis-(tert-octylimido)-bis-diisooctyldithiocarbamato)-molybdenum (VI).

4. The composition of claim 1 wherein the compound is (tert-octylN)$_2$Mo$\{S_2CN(Coco)_2\}_2$.

5. The composition of claim 1 wherein the compound is (tert-butylN)$_2$Mo$\{S_2CN(Coco)_2\}_2$.

6. The composition of claim 1 further comprising a lubricant.

7. The composition of claim 6 wherein the lubricant is a lubricating oil.

8. The composition of claim 6 further comprising at least one additional additive selected from the group consisting of dispersants, detergents, rust inhibitors, antioxidants, sulfurized olefins, thiadiazoles, metal deactivators, anti-wear agents, antifoamants, friction modifiers, seal swell agents, demulsifiers, VI improvers, and pour point depressants.

9. The composition of claim 6 further comprising at least one additional additive selected from the group consisting of alkylated diphenylamines, hindered alkylated phenols, hindered alkylated phenolic esters, sulfur-containing hindered phenolic esters, and sulfur-containing hindered alkylated phenols.

10. The composition of claim 9 wherein at least one additional additive is an alkylated diphenylamine.

11. The composition of claim 10 wherein the alkylated diphenylamine is selected from the group consisting of nonylated diphenylamine, octylated diphenylamine, styrenated diphenylamine, octylated styrenated diphenylamine, and butylated octylated diphenylamine.

12. The composition of claim 6 further comprising a member selected from the group consisting of 3,5-di-t-butyl-4-hydroxy-hydrocinnamic acid, a $C_7$-$C_9$ branched alkylester of 2,6-di-t-butyl-p-cresol, and mixtures thereof.

13. The composition of claim 6 further comprising a member selected from the group consisting of zinc dialkyldithiophosphates, zinc diaryldithiophosphates, and mixtures thereof.

14. The composition of claim 6 further comprising a mixture of at least one alkylated diphenylamine and at least one zinc dialkyldithiophosphate.

15. The composition of claim 14 wherein the mixture further comprises at least one hindered alkylated phenolic.

16. A method for reducing the coefficient of friction of a lubricant comprising adding to said lubricant a compound selected from the group consisting of bis-(tert-butylimido)-bis-diisooctyldithiocarbamato)-molybdenum (VI), bis-(tert-octylimido)-bis-diisooctyldithiocarbamato)-molybdenum (VI), (tert-octylN)$_2$Mo$\{S_2CN(Coco)_2\}_2$, and (tert-butylN)$_2$Mo$\{S_2CN(Coco)_2\}_2$.

17. The method of claim 16 wherein the compound is bis-(tert-butylimido)-bis-diisooctyldithiocarbamato)-molybdenum (VI).

18. The method of claim 16 wherein the compound is bis-(tert-octylimido)-bis-diisooctyldithiocarbamato)-molybdenum (VI).

19. The method of claim 16 wherein the compound is (tert-octylN)$_2$Mo(S$_2$(Coco)$_2$)$_2$.

20. The method of claim 16 wherein the compound is (tert-butylN)$_2$Mo(S$_2$(Coco)$_2$)$_2$.

21. The method of claim 16 wherein the lubricant is a lubricating oil.

* * * * *